United States Patent
Kamali

(10) Patent No.: US 7,413,426 B2
(45) Date of Patent: Aug. 19, 2008

(54) DENTURE FLASK COMPRESS TOOL AND PROCESS

(76) Inventor: Mirahmad Kamali, 431 N. Frederick Ave., Gaithersburg, MD (US) 20877

( * ) Notice: Subject to any disclaimer, the term of this patent is extended or adjusted under 35 U.S.C. 154(b) by 0 days.

(21) Appl. No.: 11/717,030

(22) Filed: Mar. 13, 2007

(65) Prior Publication Data

US 2007/0238070 A1    Oct. 11, 2007

Related U.S. Application Data

(60) Provisional application No. 60/790,793, filed on Apr. 11, 2006.

(51) Int. Cl.
  *A61C 13/08*    (2006.01)
(52) U.S. Cl. .............................. 425/177; 81/439; 264/17
(58) Field of Classification Search .................. 425/175, 425/177; 81/436, 439, 461; 264/17
  See application file for complete search history.

(56) References Cited

U.S. PATENT DOCUMENTS

| | | | |
|---|---|---|---|
| 663,309 A | 12/1900 | Tuttle | |
| 3,267,525 A | 8/1966 | McGowan | |
| 3,571,858 A | 3/1971 | MCGowen | |
| 4,218,205 A | 8/1980 | Beu | |
| 4,984,844 A * | 1/1991 | Tekeyan | 279/148 |
| D341,599 S | 11/1993 | Tanaka | |
| 6,978,702 B1 | 12/2005 | Diggle et al. | |
| 7,114,418 B1 | 10/2006 | Allen | |

* cited by examiner

*Primary Examiner*—Robert B Davis
(74) *Attorney, Agent, or Firm*—J. David Welsh

(57) ABSTRACT

Disclosed is a tool for turning a hex screw at the top of a denture compress containing denture flasks which comprises a hex key wrench having a shaft of finite length. Turning the hex screw in one direction causes pressure to be applied to a plate beneath it, and to the denture flasks within the compress. At one end of the shaft there is a handle perpendicular to the shaft, a T-handle. At the opposite end of the shaft a plurality of hex keys of different sizes are formed, in a contiguous relationship, the largest hex key being closest to the shaft and the smallest being furthest from the shaft. The T-handled hex key is supported by a frame which is attached to a flat base plate. The frame is perpendicular to the plane of the base plate, which has either within its surface or on its surface means for temporarily securing the dental compress thereto.

6 Claims, 3 Drawing Sheets

DENTURE FLASK COMPRESS TOOL AND PROCESS

RELATED U.S. APPLICATION DATA

This Application relies on the benefit of an earlier filing date, authorized under 35 USC 119(e), of Provisional Application Ser. No. 60-790793, filed on Apr. 11, 2006 in the U.S. Patent and Trademark Office.

BACKGROUND OF THE INVENTION

Field of the Invention

My invention relates broadly to the art of making dentures for replacing sets of natural teeth, in particular, to a denture compress tool and hexagonal key wrench which enables greater ease and safety in the step of producing the optimum pressure to denture flasks prior to and during the curing step.

SUMMARY

The steps in conventional prosthetic dentistry mostly involve first making an impression of a patient's mouth by a dentist. The impression is then sent to a dental laboratory for fabricating a denture. At the laboratory a dental technician casts a model of the mouth using the impression from the dentist, making the cast model with a composition called stone powder. After completing all necessary steps, the technician, using an articulator, sets prosthetic teeth on the stone model in alignment and in proper position. Then the prosthetic teeth are secured by hand to the model of the mouth with a wax composition to make a trial denture or dentures for the patient. The trial dentures are removed from the stone cast and sent to the dentist where they tested by the patient and dentist for fit and suitability, etc. and returned to the lab where a permanent plastic or polymer composition is substituted for the wax in the trial denture.

A permanent synthetic plastic, polymer or resin composition replacement for the wax is made by placing the trial dentures in a two-section special container called a denture flask, subsequently securing the trial dentures to the base of the flask with stone powder. Then an impression of the wax trial dentures is made using stone powder. After all investments are hardened sufficiently, the flask is subjected to a hot water treatment to soften and melt the wax. The wax is removed from the flasks, the two sections of the flask are separated, and cavities within the stone composition are formed with the prosthetic teeth held in position by the hardened stone, a plaster-like composition.

Next the cavity space is packed with an acrylic resin composition in the form of a dough in between the two sections of the flask, and thereafter, customarily, the flask is positioned within a press to squeeze out all of the excess acrylic resin composition. The next step is to cure the resin composition.

For maintaining the accuracy and fidelity of the plastic or resin denture shape during the curing process, the flask must be maintained under heat and considerable pressure. Conventionally curing is done using a compression unit called a denture compress, a rectangular frame made of bronze having at it's top a female hex screw. The screw is adapted to receive a hex key or Allen wrench insert having an outside diameter size range from about ⅜ inches to about ¾ inches in size.

The hex screw abuts a pressure plate below it. Pressure is conventionally applied to the denture flasks by turning an L-shaped hex key, or Allen wrench of about five to seven inches in length, which is inserted into the insert slot opening of the hex screw and then turned to drive the screw against the pressure plate. The technician grasps a short, removable handle, attached to one side of the denture compress near the top while turning the Allen wrench.

Compresses are commercially available in different sizes and have hex screw insert slots of different sizes, the slot sizes being about 7/16, ½ and 9/16 inches across.

This conventional method, herein described, for applying the optimum pressure to the denture flasks containing the acrylic denture forming composition is decidedly awkward, often dangerous, crude and beyond the capability of many dental technicians, especially older persons and women, for example, who generally don't have strength equal to younger people or of male technicians.

Prior to the advent of my inventive concepts, even physically adroit technicians have had to repeatedly strike the conventional L-shaped Allen wrenches with a hammer while kneeling on the floor and holding the compress by a short handle to be assured that the optimum flask pressure was obtained. Obviously, this process is awkward, and often very difficult for people with back problems or other physical impediments.

Thus, the objects of my invention are to provide a new denture compress tool and method for applying the optimum pressure to denture flasks, to simplify the denture fabrication process, to increase the overall process efficiency, to improve the occupational safety factor of technicians, and to enable people of limited physical ability to perform well as dental technicians by reducing the amount of expended energy required for obtaining the optimum pressure applied to denture flasks prior to the curing steps by providing to the art a new and improved denture compress tool and process.

Summarizing, my inventive contributions essentially comprise a hex key denture compress tool and jig for applying pressure to denture flasks which are installed within a compress unit and method of use wherein a contiguous set of hex keys of different sizes are present on one shaft.

The compress tool comprises a T-shaped hex key wrench having a plurality of contiguous male key members of a different sizes fixed to one end of a substantially straight shaft or bar of finite length. The T-handle is at the opposite end from the hex keys. The T-shaped hex key wrench may be used alone or supported in a vertical position by a support structure or frame which is secured to a base plate or platform. The base plate includes means for temporarily securing the flask compress while pressure is applied to a pressure plate at the top of the compress by turning a hex screw.

In connection with the above described inventive contributions, I have also discovered that ordinary Allen wrenches may be made to have two or three different cross-section sizes of hex keys on the same bar or shaft. In so doing, the number of Allen wrenches supplied in tool kits may be reduced by at least one half and are so adapted to be operable for turning hex screws having different female insert slot sizes. A possible limitation respecting use of such wrenches is the depth of the insert slot on the heads of hex screws. However, hex screws can be produced having greater key slot depths than are now available. This would allow the larger key on a multiple key wrench to slip into it's proper insert slot, where it snugly fits. FIG. 4 shows a side view of an Allen Wrench according to my invention. The Allen wrench shown in FIG. 4 has three functional wrench sizes on a single shaft or bar, the shaft size itself, and keys 17 and 18.

DESCRIPTION OF PRIOR ART

Design Pat. No. Des. 341,599 to Tanaka shows a design for a press, but provides no information regarding functionality in the dental lab for making dentures.

The patent to Tuttle, U.S. Pat. No. 663,309, shows a press used in forming rubber teeth in a vulcanization process. However, the process appears to be merely a molding process for rubber articles, not vulcanization, which is a process of reacting sulfur compounds with rubber latex.

The patent to McGowan, U.S. Pat. No. 3,267,525, describes a hand press and curing clamp for making dentures wherein a wrench 72, having a T-shaped handle 68 us used to turn a conventional screw 40 to apply pressure. The screw head 42 is not a hex screw, and the wrench 72 is not a hex key. Further, no mention is made of advantages or improvements achieved by using a T-shaped handle wrench.

The patent to McGowan, U.S. Pat. No. 3,571,858, describes a curing clamp for a dental flask of the conventional kind wherein a screw is driven against a pressure plate 36 to apply pressure to the dental flask.

The patent to Diggle, et al. U.S. Pat. No. 6,978,702 B1, shows a combination wrench comprising two sockets, 24 and 22, each of a different size, and one perpendicular shaft 12 comprising a hex key for turning female hex screws, but does not suggest the concept of including a plurality of hex keys of different sizes on the same shaft.

The patent to Purvis, U.S. Pat. No. 5,962,038 describes a frame FIG. 1 for holding a dental press or compress while using a hex key 25 attached to a handle 13, as shown in FIG. 2. The need for providing suitable pressure on the flasks is disclosed, col. 1, lines 46ff, however, there is no suggestion in the patent to make a modification according to the present disclosure.

The patent to Beu, U.S. Pat. No. 4,218,205 provides background information regarding denture flasks in Col. 1, and is directed to a three section flask design which is both self sealing and suitable for external compression wherein two sealing means or cap screws 31 and 33 are positioned outside of the center ⅔ of length of the flask middle section, col. 6, lines 55ff. The disclosure, however, lends no suggestion to the accomplishment of the present invention as claimed.

U.S. Pat. No. 7,114,418 B1, issued on Oct. 3, 2006, to Allen describes a faucet-seat tool having a straight elongated shaft having multiple hex-shaped or square shaped steps on one end of the shaft and having a head on the other end adapted to receive an external wrench or ratchet socket wrench into a hole having biased detent inside the head, FIG. 3, 17. Although Allen's tool is taught to be useful for extracting washer seats having different opening sizes and configurations, this disclosure does not suggest using a hex step wrench for different sized hex bolts on denture compress units. I have noted that FIGS. 1 and 4 of the patent do not faithfully picture an actual washer seat wrench in that the difference in size between the hexagonal configurations of a step wrench is not as great as that shown by the Figures.

None of these cited patents or disclosures taken either singly or in combination, is regarded to describe, anticipate or render obvious to one of ordinary skill in the art the instant invention as claimed.

DETAILED DESCRIPTION OF THE INVENTION

Figure 1:
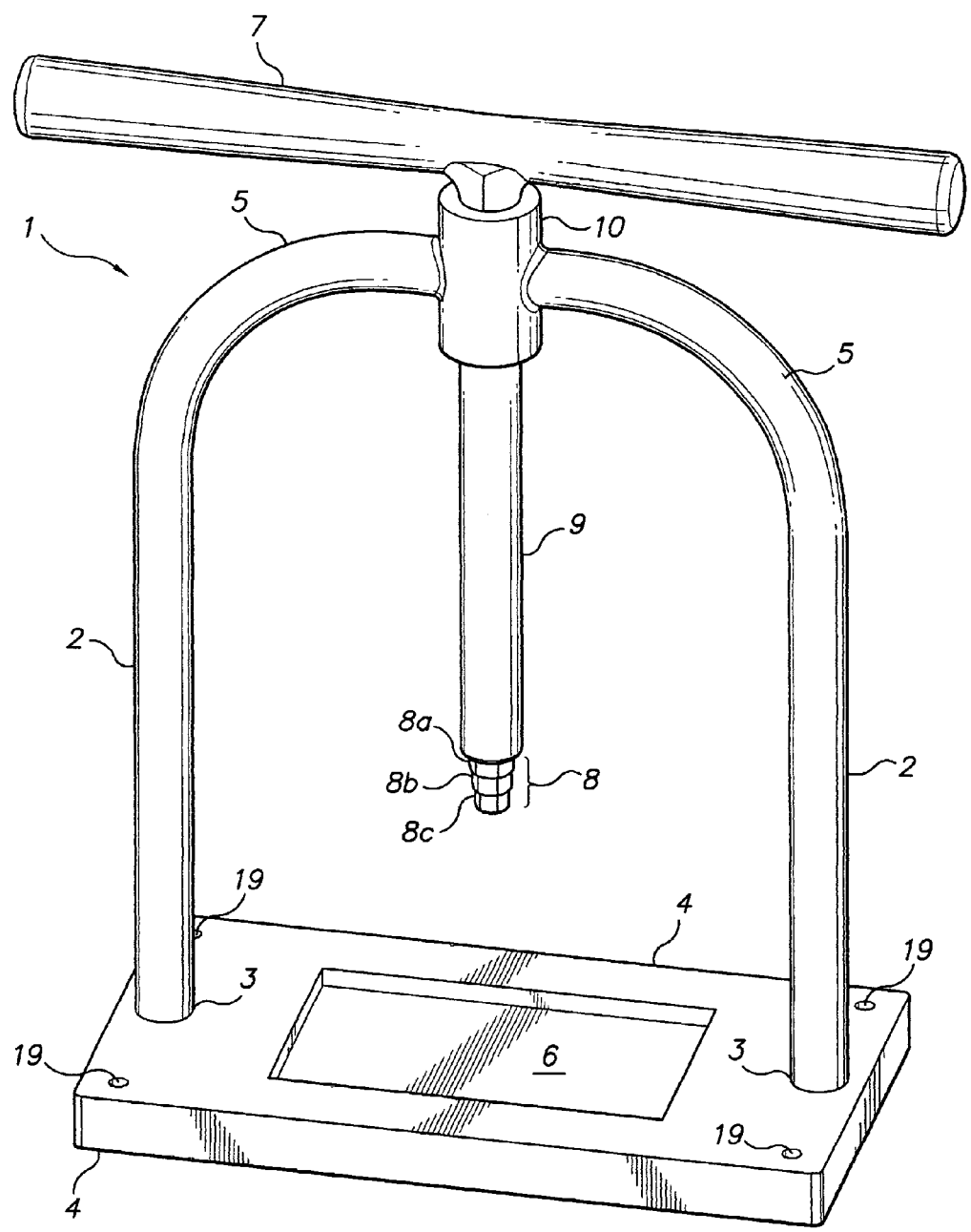
FIG. 1 is a perspective view of the general configuration of one embodiment of the denture flask press.

Referring to FIG. 1, compress press tool 1 comprises a support structure frame comprising two vertical posts 2, securely attached at two opposed locations 3 to a substantially flat, rectangular base plate 4.

The support structure frame includes contiguous third members 5 connecting the two opposite vertical post supports 2, located substantially above the base plate 4 and joined together at a sleeve or shaft guide member 10.

Base plate 4 of FIG. 1 is shown to comprise a rectangular structure having length, width and depth, the length dimension terminating at two opposing ends. The base plate 4 shown in FIG. 1 consists of a six sided structure, a top and bottom side, two longitudinal (length) sides and two lateral (width) sides.

The base plate or platform 4 may be made of any strong and durable material such as wood, metal, composite and natural or synthetic polymer material. The base plate 4 includes means 6 for holding the compress of FIG. 3 in place while hex key 8a, 8b or 8c is inserted into the hex screw 11 in the top of the flask compress shown in FIG. 3, a conventional denture compress.

Compress containment means 6 is shown in FIG. 1 as being a hollowed out area in the base plate. Other systems may be used as a containment means, such as, for example, a fence, vice grip or jig placed on top of base plate 4.

The dimensions and shape of the base plate 4 may be wrought based on the base plate's principal functions: (1) as a platform for frame supports 2 and (2) a containment means 6 or temporary securing means for denture compress units. The size of the base plate is dictated generally by the dimensions of the compress units, and the selection of the appropriate size and shape thereof is within the ability of one having ordinary skill in the art.

The shape of the top and bottom surfaces of the base plate of FIG. 1 is shown as rectangular. The base plate configuration is not limited to rectangular top and bottom surfaces, however. The top and bottom surfaces may have any suitable shape so long as the principal functions are maintained, and the top and bottom surfaces are relatively flat.

Useful dimensions for the base plate are width, 4 to 6 inches, length, 8-14 inches and thickness, ½ to ¾ inches.

Figure 3:
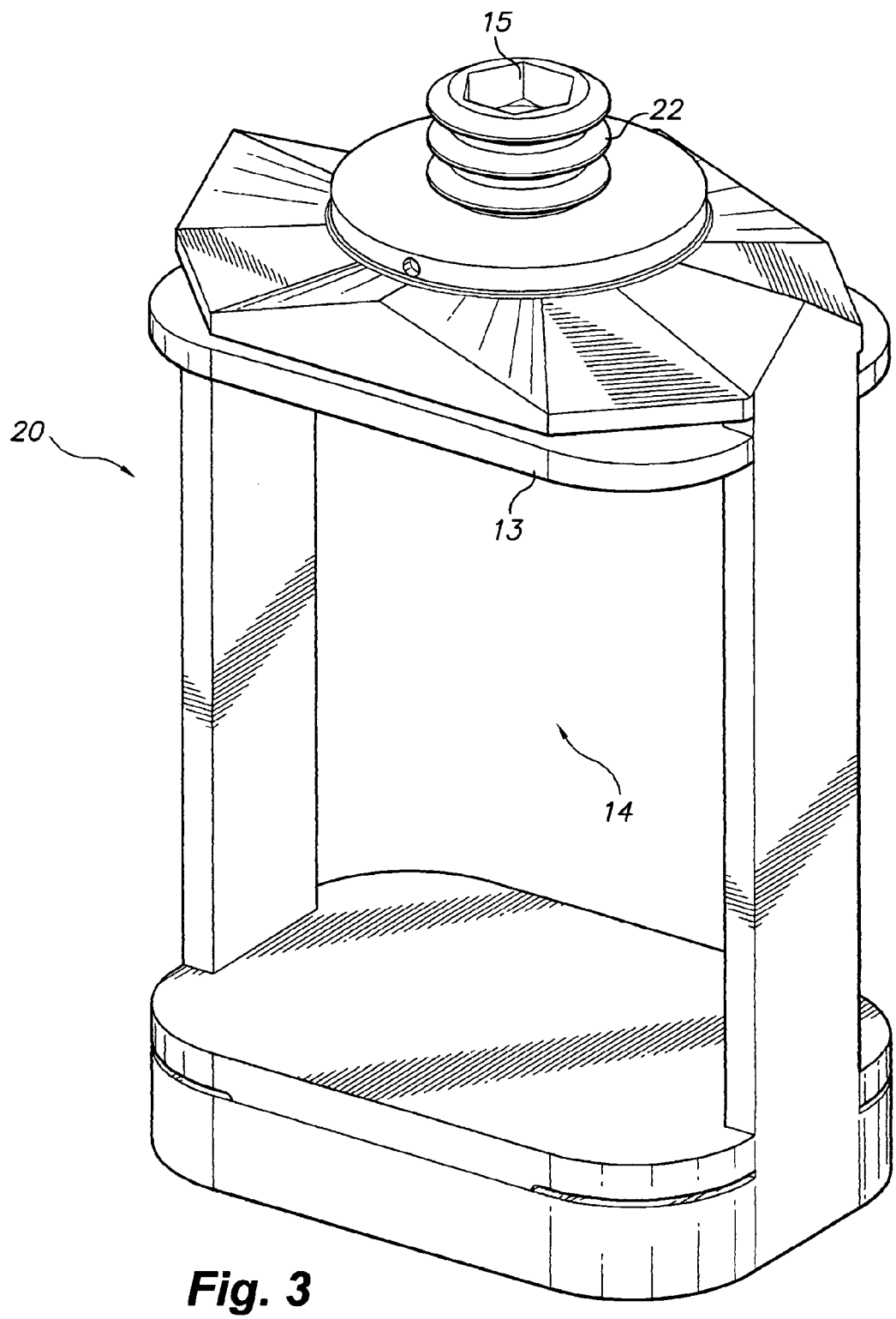
FIG. 3 is a perspective view of a conventional denture flask compress 15 having hex screw 22 at the top, absent denture flasks.

The base plate 1 must include means for temporarily holding and securing a denture compress of FIG. 3 to the plate. FIG. 1, shows a depression in the base plate's surface, a well, indentation, recess or hollowed out area 6 in approximately the center area of the base plate, functioning to secure compress 20 of FIG. 3, to prevent it from turning when torque from shaft 9 and hex key 8 is applied to the hex screw 22 of FIG. 3. The walls of the well or recess act as a break on the base of the compress preventing rotation and destabilization while the hex screw is being turned.

The well or recess 6 may be either extended completely through the base plate or only part way through the plate 4, the latter shown by FIG. 1. FIG. 1 should be regarded as illustrating or reading on both arrangements.

Referencing FIG. 1, the attachment means 3 for posts 2 may comprise a flange (not shown) through which screws or bolts are used to secure the frame to the base. Or the attachment means may comprise a welded joint or a fitted joint between the supports and base plate. In general, however, any attachment means may be used which produces a strong and secure bond, joint or connection.

FIG. 1 closely corresponds to an actual working prototype made in developing the compress tool of my inventive contributions herein in which copper pipe was used. I intend to include within the scope of my invention an embodiment wherein the compress tool 1 may comprise a unitary body. For example one where the support structures 2 and 5, sleeve 10 and the base plate 4 are made of a single material and member, as in a casting or molded metal or other material.

T-handle 7 is attached to a substantially straight shaft or bar 9, positioned and held in a vertically and rotationally adjustable relationship with support members 2 and 5 through sleeve, guide or bushing 10. Shaft 9 is movable and adjustable both vertically and rotationally through sleeve 10. It can move up and down and be easily rotated.

Figure 2:
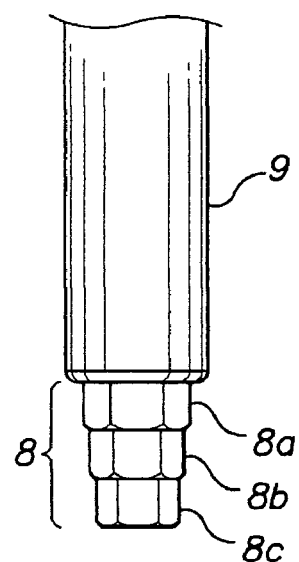
FIG. 2 is a side view of the lower end portion of shaft or bar 9 of FIG. 1, showing three contiguous hex keys 8a, 8b and 8c at the distal or end section of shaft 9.

The support members 2 are attached substantially perpendicularly with respect to the top plane of the base plate 4, and as seen in FIG. 1, are mounted on the base at two opposed positions close to the longitudinal ends of the base plate. Support structures 2 comprise two substantially vertical posts which may be configured cylindrically, flat or planar. Between support members 2 is an open area having means 6 for positioning and holding a denture flask compress At the distal end of shaft 9, a triple hex key element 8, including contiguous keys 8a, 8b and 8c, is part of shaft 9, comprising a multiple sized hex key element, the largest being closest to shaft 9 and the smallest being farthest from shaft 9. FIGS. 1 and 2 show three different sizes of hex keys on a single shaft. The individual keys have distinctly different cross-section sizes or widths as more clearly seen by FIG. 2.

FIG. 2 shows an enlarged view of a triple hex key a design 8 located at the end opposite the handle 7 attached to shaft 9, the distal segment of shaft 9. As mentioned, the shape of shaft 9 should be mostly cylindrical, however, the shape of parts of the shaft may also be hexagonal, oval or square. Obviously at the internal parts of sleeve or guide 10 should be cylindrical to allow ease of rotation.

Shown in FIG. 2 is hex key element 8, comprising contiguous keys 8a, 8b and 8c. Key 8a is larger than hex key 8b, and closer to the main shaft body than hex key 8b, while key 8c is smaller than key 8b, and farthest from the main shaft, but contiguous therewith.

The hex key wrench having multiple contiguous keys of different sizes may be manufactured by conventional metal working means, known in the art. The hex key element prototype for my compress tool was made by carefully abrading or grinding a metal shaft to form six substantially equal faces at the working end of said shaft. The individual keys were formed by the steps of abrading and measuring to produce face to face or cross-sectional width dimensions of 7/16, 1/2 and 9/16 inches. The length of each key is about equal, but may vary. Other means may be used to produce the tool of my invention, for example, casting or molding, or stamping with or without heat treatment.

The multiple contiguous hex key feature eliminates the need to have on hand a different size hex key wrench for each size of hex screw, a reduction in inventory. As mentioned herein, commercially made denture compresses are available in different sizes with different sized hex screws at the top. By virtue of my inventive concepts, one tool now fits the most common commercially available denture flasks.

Referring to FIG. 1, the top of the compress tool frame is the area closest to T-handle 7, and the bottom of the support frame is the area closest to the base plate 4. The same definition applies to shaft 9. Further, T-handle 7 is substantially perpendicular to shaft 9. The handle may be any suitable cross-sectional shape, including cylindrical, like shaft 9, shown in FIGS. 1 and 2.

Referring to FIGS. 1 and 3, shaft 9, T-handle 7 and hex keys 8 describe a triple hex key wrench for turning a hex screw 22, shown in FIG. 3, on top of a flask compress 20, in order to apply pressure against pressure plate 13 which presses against denture flasks held in the cavity or area 14 of the compress.

The denture flasks intended to be positioned within the compress are not shown in FIG. 3. However, U.S. Pat. No. 5,962,038, to Purvis is cited herein, in FIGS. 2 and 3 shows a conventional compress with dental flasks of the type contemplated in the present invention contained within the holding area of a compress. Shown are flasks 10 and 24 of FIG. 2. Additional disclosure in the Purvis patent is at col. 2, lines 60-65. The disclosure of the patent to Purvis is hereby incorporated into this specification by reference.

Referring to FIG. 1, T-handle 7, functions as a rotating lever to apply torque to shaft 9. The T-handle 7 of FIG. 1 from end to end should be at least equal in length to the length of shaft 9, or of the dimension from one side to the other of the frame where it is attached to the base plate 4, and no less than about five inches from end. The handle may be of greater length than the base plate, if desired, to provide increased torque. The determination of an appropriate length for handle 7 is a matter of routine experimentation.

The compress shown in FIG. 3, containing denture flasks, is placed under the shaft 9 and inside the recessed area 6 directly underneath the hex key element 8. As mentioned, the recessed area 6 functions as a containment means to prevent the compress, from turning or becoming unstable while applying torque to the hex screw 22. The dimensions of the recessed area are selected to be effective for preventing the turning movement of different sizes of denture compresses.

The recessed area 6, may be designed to closely conform to the shapes of the compress bases to obtain a snug fit, if desired. Also, a suitable design may comprise two contiguous containment areas to closely conform to two different sizes of compresses within the same general recess or depression.

Alternatively, the well or depression area 6 may be replaced with a metal or plastic fence or bracket arrangement, not shown, of sufficient strength, on the top surface of the base plate. The compress containing the flasks are in this case placed between brackets, jig or vice type of device. One or more of such brackets may be easily adjustable to clamp the denture compresses in place.

For safety and ease of operation, the base plate must be firmly attached to a work bench or table. Attaching the compress tool to a work bench may be accomplished by conventional means using screws, bolts or clamps. As seen in FIG. 1, holes 19, through the base plate are shown for attachment means.

The supporting frame structures 2-5 are depicted in FIG. 1 as having a curved or bowed shape. This configuration is not necessarily required, and my invention is not limited to a specific shape of the support structure. The principle requirement for the tool design is for the sleeve or shaft guide 10 to be centered between support structures 2 and be perpendicular to the plane of the base plate.

In FIG. 1, the sleeve 10 is shown as being a tube-like cylindrical structure, located at the mid-point of the top support structures 5. Sleeve 10 functions as a guide and containment means for the hex key shaft 9, having an inside diameter slightly larger than the diameter of the shaft 9, and positions and supports the hex key shaft or bar 9 in alignment with hex screw 22 of the flask compress 20 of FIG. 3 when the compress is positioned within the containment area 6, or between supports 2 of FIG. 1. The hex key shaft 9 should be made of metal for strength.

Other materials, means or designs for the sleeve or shaft guide 10 are contemplated to be within the scope of the invention. For example, the guide member 10 may comprise a circular metal ring or strong plastic ring or bushing in a design other than that of FIG. 1. If the support frame 2-5 were to be composed of a strong, flat stock material of metal or plastic, or other material such as a composite, a simple hole through the frame at the mid-point may be a suitable guide, however, such a tool may not have the stability of the design shown in FIG. 1.

The hex key shaft or bar 9 is, of course, not held fast to the guide or sleeve 10, but is easily turned and removable from containment and support guide 10. It is easily rotated about the long axis of shaft 9 or removed entirely from the support structure, and used independently thereof to turn the hex screw 22 of FIG. 3 if desired.

Respecting the T-handle 7, it is within the scope of my inventive concepts to make hex key wrench using a single contiguous member, wherein the handle or lever 7 is contiguously joined to shaft 9, as one piece, for example, a casting.

Inspection of FIG. 1, handle 7, one can see that a dental technician, using both hands on each side of the handle, can easily apply sufficient torque upon the hex screw 22 of FIG. 3, enabling compression of the denture flasks to be maintained at optimum level during the curing process.

It has been found that it is relatively easy for an average person to estimate the force necessary to be applied to each side of handle 7 to produce consistent results in the quality and accuracy of the denture, with only a limited experience of using the tool of the invention.

Further, handle 7 is not limited to a bar or shaft as shown by FIG. 1, but the inventive concept includes a disk or wheel type of lever to apply torque to shaft 4, such as those used to turn flow valves off and on. Handle 7, in effect, functionally amounts to a lever to apply torque to a female hex screw, and therefore such a lever may take any one of several forms, including a wheel or disk. In practice, a wheel or circular turning element is a lever, in its basic function, for turning a shaft.

It is customary practice in most dental labs to use a two-stage pressing process prior to the curing step. In the first pressing step, a strong cast iron or steel press having a flat plate at the top and an opening to contain individual denture flasks, not positioned within a compress, is used. This pressing step is applied to each individual flask to squeeze out excess acrylic polymer composition from within the flask. I have unexpectedly found that by using the compress tool described herein, the force generated is sufficient to both remove excess acrylic polymer composition from the flasks and to provide sufficient flask pressure for the curing operation. Thus, with my compress tool the first pressing step may be eliminated. The number of steps made prior to the curing operation is reduced, resulting in greater production efficiency.

Of course, the T-handle hex key wrench of my design could be used without the frame support so long as there are means for securing the denture compress in place with either clamps, a fence or some sort of a recessed area upon a flat surface like a table or a secured base plate, and such an embodiment is included to be within the scope of my inventive concept.

Figure 4:
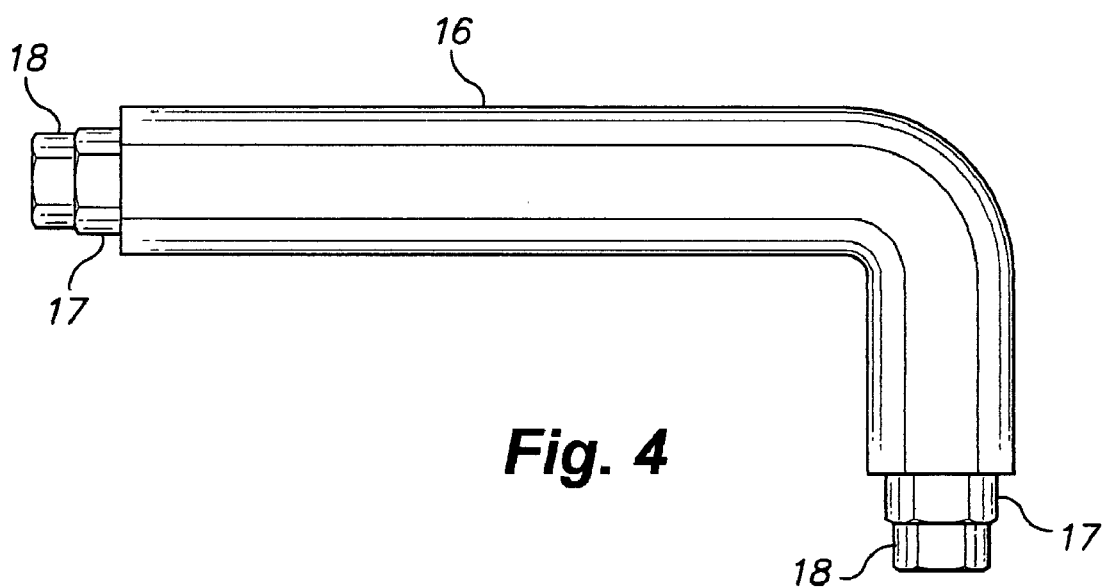
FIG. 4 shows a side view of an Allen wrench having three different dimensions of functional contiguous keys, one of which is merely an extension of the main shaft.

Further, it is my inventive concept also to provide a modified Allen wrench, as seen by FIG. 4, an L-shaped hexagonal metal bar as a main shaft, and to provide to the mechanical arts an Allen wrench design having two or three different cross-sectional sizes of keys on the same shaft at both ends of the Allen wrench. In FIG. 4, a first functional key 16 is the same cross-sectional size as the main shaft itself, a second key 17, contiguous with the shaft and first key, has a cross-section smaller than the first at the ends of the main shaft or distal positions of the shaft, and a third functional key 18, of smaller cross-section and smaller than the second at the terminus the shaft, as seen by FIG. 7. Such a tool works most effectively with hex screws having slightly deeper insert slots for the keys that those currently available. Not only can the cross-sectional size of the added keys 17 and 18 be different, but also the length of the keys can differ.

DEFINITIONS

The term "hex key" means a hexagonal or six sided rod or shaft the end of which constitutes a key which fits into a correspondingly configured screw slot, each side being approximately equal size, and the term "hex screw" applies to the configuration of a six-sided female insert for receiving a male hex key of about the same size, in the head of a threaded screw or bolt.

The term "distal" means situated away from the point of attachment or origin.

The term "T-handle" means a device wherein the junction between the handle and the functional member is about perpendicular to said functional member, as in the English letter T.

The term "contiguous" means touching or joined to one another.

The term "Allen wrench" means an L-shaped hexagonal metal bar, shaft or rod, either end of which fit's a hexagonal socket of a screw or bolt.

What is claimed as the invention is:

1. A denture compress tool for applying pressure to a compress containing denture flasks for making dentures, said tool comprising a substantially flat base plate having secured thereto a frame, said frame positioned substantially perpendicular to the top of said base plate, the frame comprising two opposing support members and a connecting third support member above the base plate, and a containment and a sleeve guide means having a cylindrical tubular structure at the mid-point of said frame, within which is positioned a cylindrical shaft, also positioned substantially perpendicularly to the base plate, and having at the top end thereof a T-lever for turning said shaft, wherein said lever and said shaft comprise a single contiguous, one piece member, having a plurality of contiguous hex keys of different sizes at the distal end of said shaft, and means contained within the base plate for temporarily holding a denture flask compress to keep it from turning while torque is applied to a hex screw at the top of said compress.

2. The denture compress tool defined by claim 1 wherein the length of the T-lever is at least equal to the dimension from one side of the frame to the other where the frame is attached to the base plate.

3. The denture compress tool of claim 1 wherein the number of contiguous hex keys is from two to three.

4. The compress tool defined by claim 1 wherein the contiguous hex keys are three in number, and wherein the largest key is in inches about 9/16, the middle key about 8/16 and the smallest key is about 7/16 inches.

5. In a method for making dentures involving applying pressure to denture flasks contained within a denture compress and then subjecting said flasks to a curing step, the improvement comprising turning a hex screw located at the top of the compress to apply significant pressure to the denture flasks with the denture compress tool defined by claim 1.

6. A modified Allen Wrench comprising a finite hexagonal shaft, said shaft having at both ends a first hex key of one cross-sectional size which is the shaft itself, and a second hex key contiguously attached to said first hex key having a cross sectional size different from that of said first key, about the same size thereof, and a third hex key of a smaller size than said second key and contiguous with the second key and further from the shaft.

* * * * *